(12) United States Patent
Motoyuki et al.

(10) Patent No.: US 6,717,009 B2
(45) Date of Patent: Apr. 6, 2004

(54) METHOD FOR MAKING HIGH-PURITY NAPHTHALENEDICARBOXYLIC ACID

(75) Inventors: Masahiro Motoyuki, Kobe (JP); Tomoki Uemura, Kobe (JP); Koji Yamamoto, Kobe (JP)

(73) Assignee: Kabushiki Kaisha Kobe Seiko Sho (Kobe Steel, Ltd.), Kobe (JP)

( * ) Notice: Subject to any disclaimer, the term of this patent is extended or adjusted under 35 U.S.C. 154(b) by 0 days.

(21) Appl. No.: 10/265,401

(22) Filed: Oct. 7, 2002

(65) Prior Publication Data

US 2003/0078452 A1 Apr. 24, 2003

(30) Foreign Application Priority Data

Oct. 23, 2001 (JP) ......................... 2001-324455

(51) Int. Cl.$^7$ ................ C07C 51/42; C07C 63/33; C07C 51/16
(52) U.S. Cl. .............. 562/486; 562/417; 562/416; 562/487; 562/488
(58) Field of Search ................ 562/417, 416, 562/487, 488, 486

(56) References Cited

U.S. PATENT DOCUMENTS 3,671,578 A * 6/1972 Ogata et al. ............ 562/488
5,256,817 A * 10/1993 Sikkenga et al. ......... 562/487
5,616,792 A * 4/1997 Bartos et al. ............ 562/486

* cited by examiner

Primary Examiner—Alan L. Rotman
Assistant Examiner—Taylor Oh
(74) Attorney, Agent, or Firm—Oblon, Spivak, McClelland, Maier & Neustadt, P.C.

(57) ABSTRACT

A high-purity naphthalenedicarboxylic acid is produced by a method including Steps [1] and [2]: In Step [I], a raw mixture of crude terephthalic acid and crude naphthalenedicarboxylic acid is dissolved into high-temperature high-pressure water to form a dibasic acid solution wherein the crude naphthalenedicarboxylic acid content is 0.1 to 10 mass percent of the crude terephthalic acid content, the dibasic acid solution is brought into contact with hydrogen in the presence of a catalyst. In Step [II], the resultant in the dibasic acid solution is crystallized by multiple stages while the temperature and the pressure are reduced for each stage, and acid mixtures containing enriched naphthalenedicarboxylic acid or enriched terephthalic acid are obtained by solid-liquid separation.

14 Claims, 3 Drawing Sheets

METHOD FOR MAKING HIGH-PURITY NAPHTHALENEDICARBOXYLIC ACID

BACKGROUND OF THE INVENTION

1. Field of the Invention

The present invention relates to a method for making a high-purity naphthalenedicarboxylic acid at low costs and a high efficiency. The resulting high-purity naphthalenedicarboxylic acid is useful as a raw material for high-performance polyester resins, i.e. polyethylene naphthalate (hereinafter referred to as PEN) and polybutylene naphthalate (hereinafter referred to as PBN). Furthermore, a dibasic acid mixture of terephthalic acid and 0.5 to 10 mass percent naphthalenedicarboxylic acid is used for preparation of a copolyester of polyethylene terephthalate (hereinafter referred to as PET) and PEN, which exhibits higher gas barrier and higher ultraviolet absorption than PET homopolymer.

2. Description of the Related Art

As is well known, PEN has excellent properties, i.e. high mechanical strength, high heat resistance, and high gas barrier; hence, PEN has a variety of actual and potential applications, for example, videotapes and video films for long time recording, advanced photo systems (APSs), heat resistant containers, tire cords, films, and bottles.

In addition, recent prospective applications of PBN are electrical insulating materials and automobile parts. A copolymer of PET and 0.5 to 10 mass percent PEN exhibits gas barrier and ultraviolet absorption, which are significantly higher than those of a PET homopolymer. Such characteristics are in favor of applications to bottles and films.

PEN, PBN, and PET/PEN copolymers are very expensive because no method for making a high-purity naphthalenedicarboxylic acid as a raw material at low costs and high efficiency is established. Accordingly, such disadvantages preclude commercial production of these polymers regardless of the above-mentioned advantages.

A well-known method for making a naphthalenedicarboxylic acid is oxidation of a dialkylnaphthalene such as dimethylnaphthalene with molecular oxygen in the presence of a catalyst, for example, Co, Mn, or Br. As shown in FIG. 1, however, the crude naphthalenedicarboxylic acid prepared by this method contains many impurities: tricarboxylic acids, i.e. trimellitic acid (TMA); dicarboxylic acids, i.e. bromonaphthalenedicarboxylic acid (Br-NDA); and monocarboxylic acid, i.e. formylnaphthoic acid (FNA), methylnaphthoic acid (MNA), and naphthoic acid. These impurities significantly impair physical properties of the PEN, PBN, and PET/PEN copolymers and cause coloring of polyester products.

Such problems can be easily understood by comparing with a method for making high-purity terephthalic acid. Terephthalic acid is prepared by oxidation of p-xylene in an acetic acid solvent. Crude terephthalic acid prepared by this process contains an impurity 4-carboxybenzaldehyde (4-CBA) that corresponds to the FNA in the crude naphthalenedicarboxylic acid.

Also, 4-CBA adversely affects physical properties of PET and cannot be removed from terephthalic acid by a solid-liquid separation process because both are contained in the solid phase. Hence, 4-CBA is removed as follows: Crude terephthalic acid is dissolved into high-temperature, high-pressure water typically at 80 atm pressure and 290° C. and is reduced in the presence of a Pd/C catalyst into p-toluic acid, which is soluble in the liquid phase.

However, this process cannot be applied to purification of the crude naphthalenedicarboxylic acid because the naphthalenedicarboxylic acid is not substantially dissolved into the above high-temperature, high-pressure water. Furthermore, no other ordinary solvents that can dissolve the naphthalenedicarboxylic acid are found. Accordingly, it is very difficult to purify the crude naphthalenedicarboxylic acid.

Several methods for purifying a crude naphthalenedicarboxylic acid have been disclosed in order to solve these problems.

For example, Japanese Unexamined Patent Application Publication No. 10-53557 discloses a method for making the corresponding high-purity naphthalenedicarboxylic acid including reaction of a crude naphthalenedicarboxylic acid with an amine in a mixed solvent containing water, acetone, and the amine to form an amine salt of the naphthalenedicarboxylic acid, crystallization and separation of the resultant, and heating of the crystallized resultant in the presence of water to remove amine by evaporation.

Japanese Unexamined Patent Application Publication No. 7-304705 discloses a method for making the corresponding crystallized high-purity naphthalenedicarboxylic acid including dissolution of a crude naphthalenedicarboxylic acid into supercritical or subcritical water containing one of the entrainers, such as oxygen-containing organic solvents, i.e. alcohols, ketones, and ethers, cooling the solution to crystallize the target compound.

U.S. Pat. No. 5,256,817 discloses a method for making a high-purity naphthalenedicarboxylic acid by hydrogenation in the presence of Pd/C catalyst in a mixed solvent of acetic acid and water (about 90:10).

Each of these methods, however, requires an expensive mixed solvent and many hours for recovering the solvent; hence, these methods are still not suitable for commercial production of the high-purity naphthalenedicarboxylic acid.

SUMMARY OF THE INVENTION

An object of the present invention is to provide a method for making a mixture of high-purity terephthalic acid and high-purity naphthalenedicarboxylic acid from a raw mixture of crude terephthalic acid and crude naphthalenedicarboxylic acid using a known purification facility for terephthalic acid at high efficiency and low production costs.

Another object of the present invention is to provide a method for making high-purity naphthalenedicarboxylic acid at high efficiency using the same facility.

A method for making a high-purity naphthalenedicarboxylic acid according to the present invention comprises:

Step [I] of dissolving a raw mixture of crude terephthalic acid and crude naphthalenedicarboxylic acid into high-temperature high-pressure water to form a dibasic acid solution wherein the crude naphthalenedicarboxylic acid content is 0.1 to 10 mass percent of the crude terephthalic acid content, and bringing the dibasic acid solution into contact with hydrogen in the presence of a catalyst; and Step [II] of crystallizing the resultant in the dibasic acid solution by multiple stages while reducing the temperature and the pressure for each stage and obtaining acid mixtures containing enriched naphthalenedicarboxylic acid or enriched terephthalic acid by solid-liquid separation.

In this method, only the acid mixture containing enriched naphthalenedicarboxylic acid may be separated in Step [II]. The purity of the resulting naphthalenedicarboxylic can be further increased by washing the acid mixture containing enriched naphthalenedicarboxylic acid separated in Step [II] with an alcoholic solvent.

Preferably, the alcoholic solvent comprises at least one selected from the group consisting of methyl alcohol, ethyl alcohol, and isopropyl alcohol. These alcohols may be used alone or in combination.

The temperature and pressure in Step [1] depend on the purity of the crude naphthalenedicarboxylic acid, the purity of the crude terephthalic acid, the ratio thereof in the mixture, and the target content of naphthalenedicarboxylic acid in the purified mixture. Preferably, the dibasic acid solution is brought into contact with hydrogen at a temperature in the range of 250° C. to 320° C. and a pressure of 40 to 130 atm pressure in Step [1].

Preferably, the amount of the hydrogen supplied during the hydrogenation in Step [1] is in the range of 1 to 10 mole percent of the total of the terephthalic acid and the naphthalenedicarboxylic acid in the raw mixture. In the hydrogenation, the catalyst preferably comprises at least one Group VIII metal that is supported on a carbon support. Preferably, the Group VIII metal is selected from Pd and Ru. Preferably, the amount of the Group VIII metal is 0.03 to 5.0 mass percent of the carbon support.

In this method, the raw mixture of crude terephthalic acid and crude naphthalenedicarboxylic acid may be prepared by simultaneously oxidizing p-xylene and 2.6-dimethylnaphthalene.

In the present invention, crude naphthalenedicarboxylic acid can be purified by hydrogenation of a mixture of crude naphthalenedicarboxylic acid and crude terephthalic acid and by multistage crystallization of the resultant using a known purification facility for crude terephthalic acid. Since a polyester copolymer polymerized using naphthalenedicarboxylic acid shows improved gas barrier and ultraviolet absorbability, the purified mixture of terephthalic acid and naphthalenedicarboxylic acid prepared by this method can be used as a dibasic acid mixture for forming the polyester copolymer having high gas barrier and high ultraviolet absorbability.

DESCRIPTION OF THE PREFERRED EMBODIMENTS

In the present invention, a method for making a high-purity naphthalenedicarboxylic acid includes the following steps:

Step [I] of dissolving a mixture of crude terephthalic acid and 0.1 to 10 mass percent of the corresponding crude naphthalenedicarboxylic acid into high-temperature, high-pressure water and bringing the solution in contact with hydrogen in the presence of catalyst;

Step [II] of crystallizing the resultant by multiple stages while reducing the temperature and the pressure and obtaining an acid mixture containing enriched naphthalenedicarboxylic acid and terephthalic acid by solid-liquid separation.

As described above, there are many plants for producing high-purity terephthalic acid, and a typical plant has a production capacity ranging from 200,000 to 350,000 tons per year. The outline of the plant for producing terephthalic acid is as follows:

Crude terephthalic acid produced by oxidation of p-xylene contains a trace amount of 4-CBA, as described above. Since this impurity cause appreciable deterioration of physical properties of polyesters prepared using the terephthalic acid, this must be removed as much as possible. However, 4-CBA cannot be removed by solid-liquid separation because 4-CBA is present together with terephthalic acid in the solid phase.

Hence, 4-CBA is removed as follows: Crude terephthalic acid is dissolved into high-temperature, high-pressure water typically at 80 atm pressure and 290° C. and is reduced in the presence of a Pd/C catalyst into p-toluic acid, which is soluble in the liquid phase. After hydrogenation, a high-purity terephthalic acid slurry is prepared by solid-liquid separation including five to six stages while reducing the pressure and temperature. High-purity terephthalic acid is recovered by high-pressure centrifugal separation, normal-pressure centrifugal separation, and drying steps.

Figure 2:
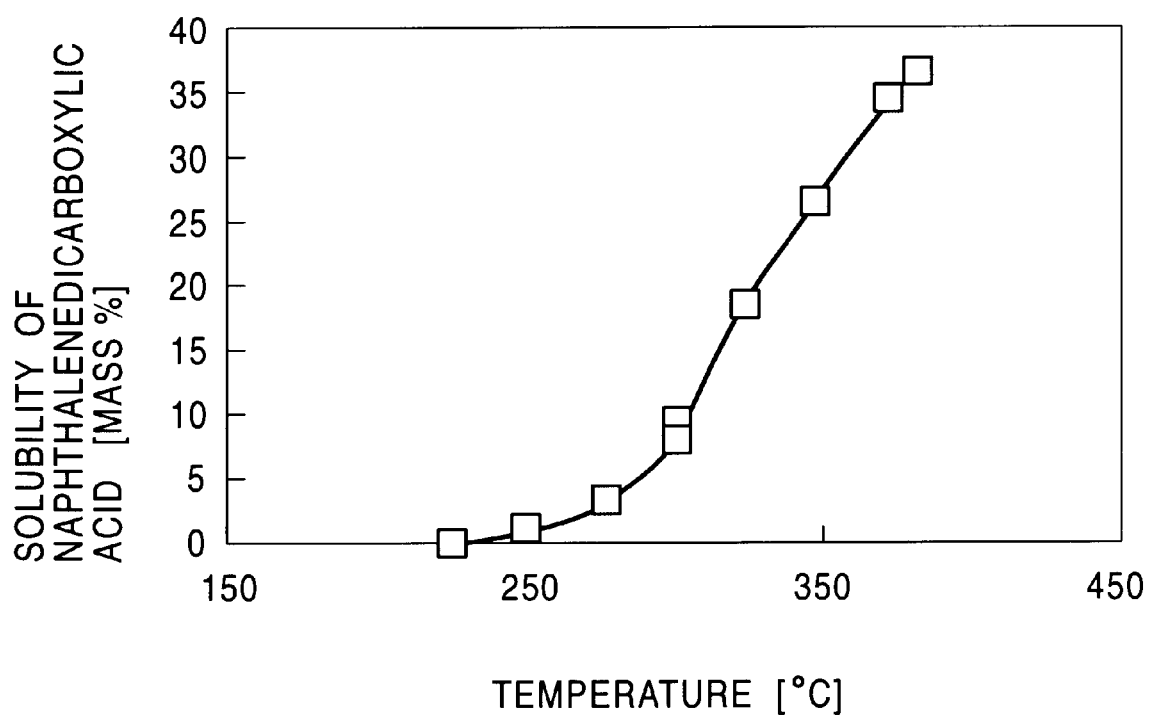
FIG. 2 is a graph illustrating the relationship between the solubility of a naphthalenedicarboxylic acid in water and the temperature.

FIG. 2 shows a solubility curve of naphthalenedicarboxylic acid in water at 80 atm pressure. According to the graph, 1 to 5 mass percent naphthalenedicarboxylic acid can be dissolved in water under the above high-temperature, high pressure condition for dissolving the terephthalic acid. When 1 to 5 mass percent of crude naphthalenedicarboxylic acid is preliminarily added to crude terephthalic acid, the resulting high-purity terephthalic acid also contain 1 to 5 mass percent of high-purity naphthalenedicarboxylic acid. A PET/PEN copolymer prepared by using the high-purity terephthalic acid containing high-purity naphthalenedicarboxylic acid contains a corresponding PEN component and exhibits high ultraviolet absorbability.

The preferred embodiments of the present invention will now be described in further detail with reference to the attached drawings. However, it is to be understood that the invention is not intended to be limited to the specific embodiments, and variations may be made by without departing from the spirit and scope of the invention.

Figure 3:
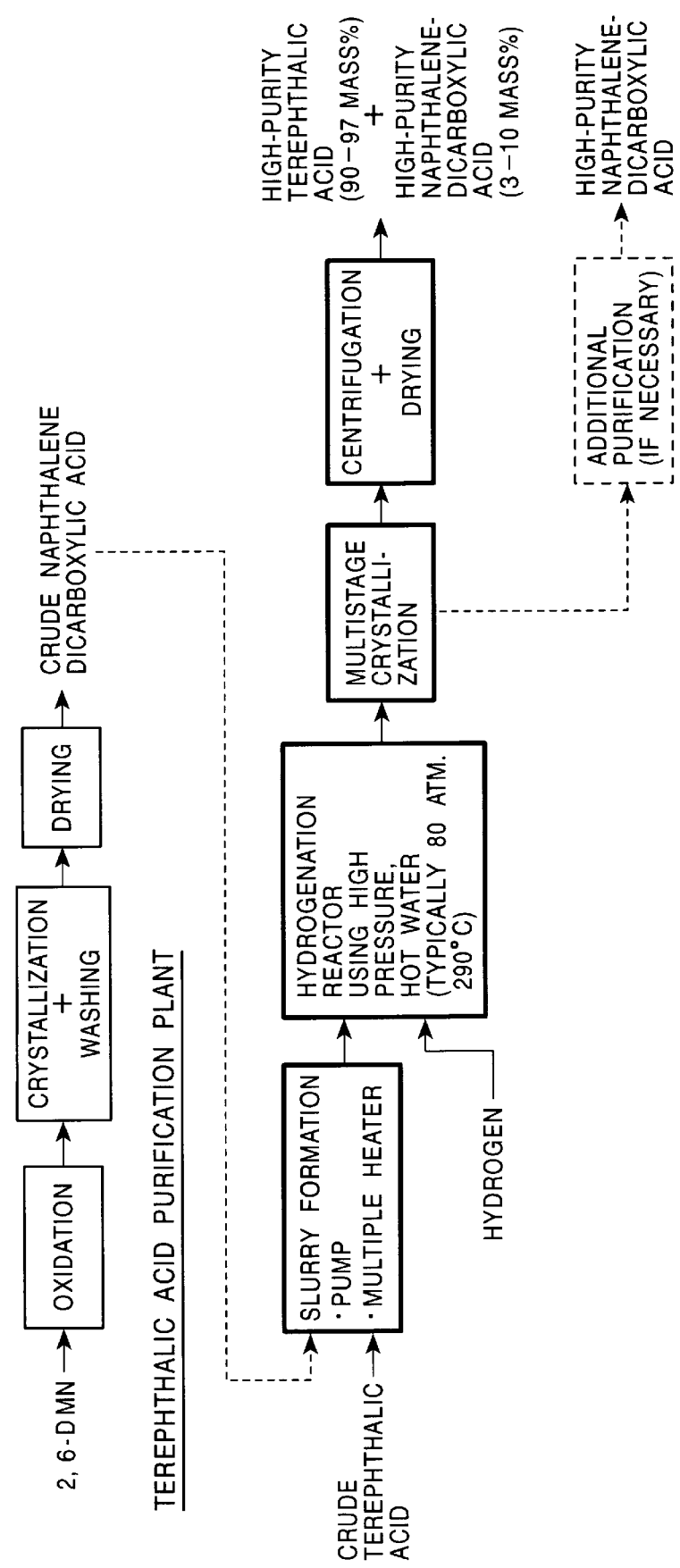
FIG. 3 is a flow chart illustrating a method according to the present invention.

FIG. 3 is an outline flow chart showing simultaneous purification of crude terephthalic acid and crude naphthalenedicarboxylic acid using a known purification plant for crude terephthalic acid. A production line of crude naphthalenedicarboxylic acid connects with the upstream side of the purification plant for the crude terephthalic acid, so that the crude naphthalenedicarboxylic acid is introduced to the purification plant for the crude terephthalic acid. The crude terephthalic acid and naphthalenedicarboxylic acid are simultaneously purified in the purification plant.

As shown in FIG. 3, 2,6-dimethylnaphthalene (2,6-DMN) is oxidized, and the resulting naphthalenedicarboxylic acid is crystallized, washed with a solvent, and dried to remove most parts of unreacted components and byproducts. As a result, crude naphthalenedicarboxylic acid is prepared. The crude naphthalenedicarboxylic acid is used as a starting material in the present invention.

Figure 1:
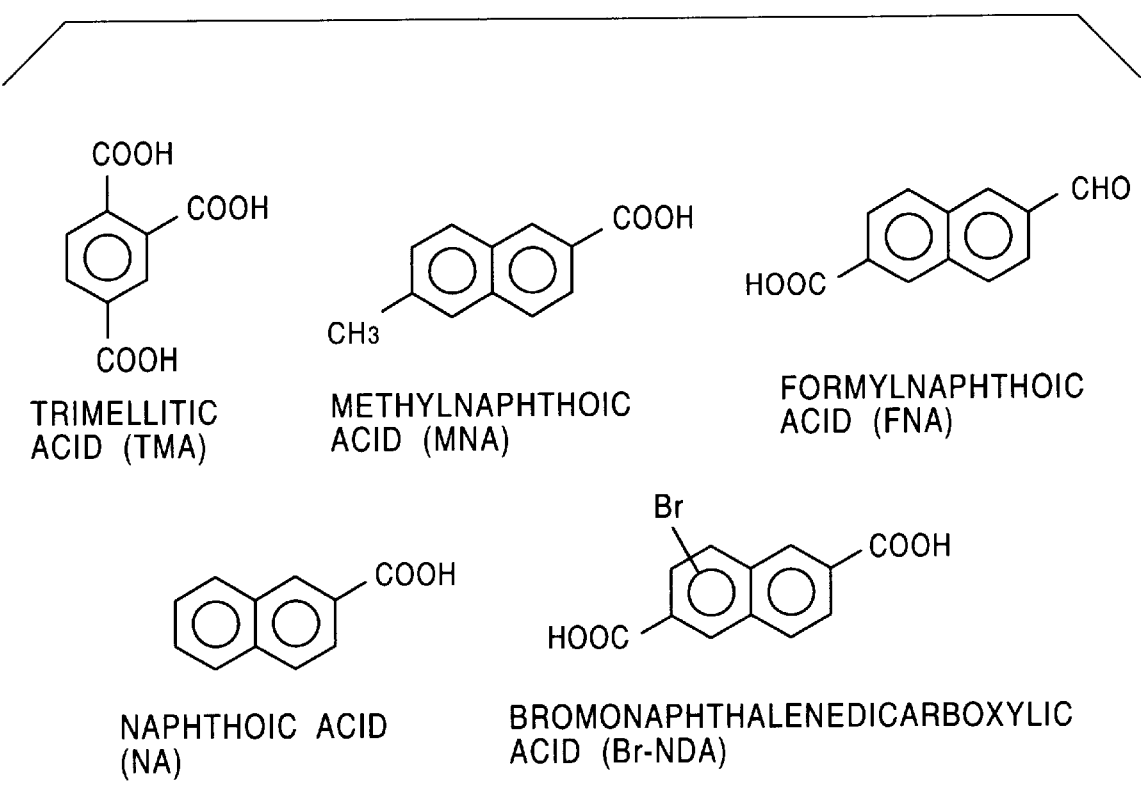
FIG. 1 shows byproducts (impurities) in a crude naphthalenedicarboxylic acid.

As shown in FIG. 1, the crude naphthalenedicarboxylic acid contains many impurities. Among these, formylnaphthoic acid having a carbonyl group cannot be easily removed and adversely affects physical properties of a final polyester product. Also, 4-CBA having a carbonyl group contained in the crude terephthalic acid adversely affects physical properties of the final polyester product.

Hence, the crude terephthalic acid and an adequate amount of crude naphthalenedicarboxylic acid are supplied to a hydrogenation purification line for crude terephthalic acid, and a slurry of the crude mixture is formed using an adequate amount of water and a multistage heater. The slurry is supplied into a hydrogenation reactor to hydrogenate the formylnaphthoic acid and 4-CBA in the crude mixture under a high-temperature, high-pressure condition. These undesirable impurities are reduced into methylnaphthoic acid and 4-carboxytoluene.

Both methylnaphthoic acid and 4-carboxytoluene have higher solubility in water than terephthalic acid and naphthalenedicarboxylic acid. During multistage crystallization using an aqueous solvent, the methylnaphthoic acid and 4-carboxytoluene are dissolved into the aqueous solvent while the terephthalic acid and naphthalenedicarboxylic acid having low solubility in water are crystallized. The crystallized product is separated from the liquid phase and dried to form a high-purity dibasic acid mixture of terephthalic acid (for example, 90 to 97 mass percent) and naphthalenedicarboxylic acid (for example, 3 to 10 mass percent) that substantially does not contain formylnaphthoic acid and 4-CBA. The high-purity dibasic acid mixture is suitable for a raw material for polyester.

In the above process, the ratio of the crude terephthalic acid to the crude naphthalenedicarboxylic acid is not limited in the present invention. Preferably, the crude naphthalenedicarboxylic acid content in the crude terephthalic acid is in the range of 0.1 to 10 mass percent in order to prepare a raw material for polyester containing a suitable amount of naphthalenedicarboxylic acid by means of the difference in solubility.

When the crude naphthalenedicarboxylic acid content in the raw material is less than 0.1 mass percent, this process is substantially the same as a known purification process for crude terephthalic acid. Such a raw material does not meet the purpose of the present invention, purification of crude terephthalic acid in the presence of crude naphthalenedicarboxylic acid. Furthermore, the naphthalenedicarboxylic acid content in the resultant is too low to produce a polyester having high ultraviolet absorbability.

When the crude naphthalenedicarboxylic acid content in the raw material exceeds 10 mass percent, the hydrogenation purification efficiency remarkably decreases; hence, byproducts cannot be sufficiently removed.

In the present invention, the crude naphthalenedicarboxylic acid content in the raw material is more preferably in the range of 0.1 to 10 mass percent and most preferably 0.2 to 5.0 mass percent. In such a naphthalenedicarboxylic acid content, the objects of the present invention are more effectively achieved: The crude terephthalic acid and the crude naphthalenedicarboxylic acid can be more readily purified in the same process, and the resulting dibasic acid mixture has a preferable composition for obtaining a polyester having superior properties.

The present invention is characterized in that byproducts inevitably formed in the processes for producing the target dicarboxylic acids are removed from the mixture of the crude terephthalic acid and naphthalenedicarboxylic acid to prepare a bibasic acid mixture of high-purity terephthalic acid and high-purity naphthalenedicarboxylic acid. In the multistage crystallization step after the hydrogenation in the flow chart shown in FIG. 3, naphthalenedicarboxylic acid having lower solubility is preferentially crystallized at the first high-temperature, high-pressure crystallization stage. By utilizing the difference in solubility, as shown by broken lines in FIG. 3, only high-purity naphthalenedicarboxylic acid can be prepared in the first stage of the multistage purification step.

When crystallization of the naphthalenedicarboxylic acid is controlled to a proper level by adjusting the temperature and pressure in each stage of the multistage purification step, the naphthalenedicarboxylic acid content in the crystals can be controlled to a desired level. When the temperature and pressure are gradually decreased on every stage of the multistage purification step, the naphthalenedicarboxylic acid content in the crystals will vary on every stage.

For example, the pressure is controlled within the range of 2 to 90 atm pressure and the temperature is controlled within the range of 140° to 300° C. in the multistage purification step to determine the naphthalenedicarboxylic acid content in the resulting crystals. Consequently, this process can produce a dibasic acid mixture of terephthalic acid and a desired amount of naphthalenedicarboxylic acid according to required properties, such as ultraviolet absorbability, for a raw material for polyester.

In FIG. 3, the naphthalenedicarboxylic acid-enriched crystals prepared in the first stage of the multistage purification step can be further purified by, for example, alcohol washing, if necessary, in order to obtain high-purity naphthalenedicarboxylic acid crystals. Similarly, the dibasic acid mixture containing high-purity terephthalic acid and high-purity naphthalenedicarboxylic acid prepared by the multistage purification, centrifugal, and drying steps can be further purified, if necessary, to obtain a higher-purity dibasic acid mixture.

Examples of preferred solvents used in the purification step include alcohols. Methyl alcohol, ethyl alcohol, and isopropyl alcohol are more preferable. These alcohols may be used alone or in combination.

As described above, in the hydrogenation step shown in FIG. 3, formylnaphthoic acid and 4-CBA, undesired byproducts formed in the processes for producing the crude terephthalic acid and crude naphthalenedicarboxylic acid, are reduced into water-soluble methylnaphthoic acid and 4-carboxytoluic acid. If this hydrogenation step is performed under severer conditions, terephthalic acid and naphthalenedicarboxylic acid will also be partially reduced, and the yield of the target materials will decrease. Thus, the hydrogenation conditions are preferably determined so as to maintain a high yield of the terephthalic acid and naphthalenedicarboxylic acid as much as possible and to reduce undesired formylnaphthoic acid and 4-CBA more effectively into methylnaphthoic acid and 4-carbyxyltoluene.

In preferable conditions in the hydrogenation step, the temperature is in the range of 250° C. to 320° C. and more preferably in the range of 280° C. 320° C., and the pressure is in the range of 40 to 130 atm pressure and more preferably in the range of 70 to 130 atm pressure. The amount of hydrogen supplied in the hydrogenation step is preferably in the range of 1 mole percent to 10 mole percent of the total of the crude terephthalic acid and crude naphthalenedicarboxylic acid in the fed components. A smaller amount of hydrogen or a lower temperature or pressure causes insufficient reduction and thus insufficient removal of undesirable components. A higher amount of hydrogen or a higher temperature or pressure causes undesired reduction and thus a decrease in yield of the terephthalic acid and naphthalenedicarboxylic acid.

Effective hydrogenation catalysts used in the hydrogenation step are Group VIII metals. Preferably, at least one Group VIII metal is supported on carbon. More preferable Group VIII metals are Pd and Ru. The amount of the Group VIII metal supported on carbon is preferably in the range of 0.03 to 5.0 mass percent and more preferably 0.03 to 3.0 mass percent of the carbon support in order to prevent oxidation of terephthalic acid and naphthalenedicarboxylic acid and to facilitate reduction of undesirable byproducts.

In the present invention, as described above, undesirable byproducts are simultaneously removed from a mixture of crude terephthalic acid and crude naphthalenedicarboxylic acid fed, and a dibasic acid mixture of high-purity terephthalic acid and high-purity naphthalenedicarboxylic acid is produced using a known purification plant for crude terephthalic acid. Alternatively, high-purity naphthalenedicarboxylic acid is isolated from the crude mixture. Thus, crude terephthalic acid and crude naphthalenedicarboxylic acid that are prepared by known processes can be used in the present invention.

However, as shown in FIG. 3, a production line of crude naphthalenedicarboxylic acid preferably connects with the upstream side of a purification plant for crude terephthalic acid. Since the crude naphthalenedicarboxylic acid produced in its production line is supplied to the purification line for the crude terephthalic acid, steps of from preparation to purification of the crude terephthalic acid or naphthalenedicarboxylic acid can be continuously performed in this combined facility. A buffer reservoir for the crude naphthalenedicarboxylic acid may be provided in the production line so that the amount of the crude naphthalenedicarboxylic acid to be supplied is adjusted.

What is claimed is:

1. A method for making a high purity naphthalenedicarboxylic acid comprising:

Step [I]: dissolving a raw mixture of crude terephthalic acid and crude naphthalenedicarboxylic acid into high-temperature high-pressure water to form a dibasic acid solution wherein the crude naphthalenedicarboxylic acid content is 0.1 to 10 weight percent of the crude terephthalic acid content, and bringing the dibasic acid solution into contact with hydrogen in the presence of a catalyst of at least one Group VIII noble metal; and Step [II]: crystallizing the resultant treated dibasic acid mixture from solution in multiple stages while reducing the temperature and the pressure for each stage and obtaining acid mixtures containing enriched naphthalenedicarboxylic acid and/or enriched terephthalic acid by solid-liquid separation.

2. The method for making a high purity naphthalenedicarboxylic acid according to claim 1, wherein only the acid mixture containing enriched naphthalenedicarboxylic acid is separated in said Step [II].

3. The method for making a high purity naphthalenedicarboxylic acid according to claim 2, wherein the acid mixture containing enriched naphthalenedicarboxylic acid is separated in said Step [II] and is washed with an alcoholic solvent.

4. The method for making a high purity naphthalenedicarboxylic acid according to claim 3, wherein the alcoholic solvent is at least one solvent selected from the group consisting of methyl alcohol, ethyl alcohol; and isopropyl alcohol.

5. The method for making a high purity naphthalenedicarboxylic acid according to claim 1, wherein the dibasic acid solution is brought into contact with hydrogen at a temperature in the range of 250° C. to 320° C. and a pressure of 40 to 130 atm in said Step [I].

6. The method for making a high purity naphthalenedicarboxylic acid according to claim 1, wherein the amount of hydrogen in said Step [I] is in the range of 1 to 10 mole percent of the total of the terephthalic acid and the naphthalenedicarboxylic acid in the raw mixture.

7. The method for making a high purity naphthalenedicarboxylic acid according to claim 1, wherein the catalyst of at least one Group VIII noble metal is supported on a carbon support.

8. The method for making a high purity naphthalenedicarboxylic acid according to claim 7, wherein said at least one Group VIII metal is selected from the group consisting of Pd and Ru.

9. The method for making a high purity naphthalenedicarboxylic acid according to claim 7, wherein the amount of said at least one Group VIII metal is 0.03 to 5.0 weight percent of the carbon support.

10. The method for making a high purity hnaphthalenedicarboxylic acid according to claim 1, wherein the raw mixture of crude terephthalic acid and crude naphthalenedicarboxylic acid is prepared by simultaneously oxidizing p-xylene and 2,6-dimethylnaphthalene.

11. The method for making a high purity naphthalenedicarboxylic acid according to claim 1, wherein said temperature ranges from 280° C. to 320° C. and said pressure ranges from 70 to 130 atm.

12. The method for making a high purity naphthalenedicarboxylic acid according to claim 9, wherein the amount of Group VIII metal of the catalyst ranges from 0.03 to 5.0 wt % of the carbon support.

13. The method for making a high purity naphthalenedicarboxylic acid according to claim 12, wherein the amount of Group VIII metal of the catalyst ranges from 0.03 to 3.0 wt % of the carbon support.

14. The method for making a high purity naphthalenedicarboxylic acid according to claim 1, wherein the amount of crude naphthalenedicarboxylic acid ranges from 0.2 to 5.0 weight percent.

* * * * *